(12) United States Patent
Fryers et al.

(10) Patent No.: US 10,466,505 B2
(45) Date of Patent: Nov. 5, 2019

(54) CONVERGENCE-SENSING ELECTRO-ACTIVE ACCOMMODATING LENS

(71) Applicant: Novartis AG, Basel (CH)

(72) Inventors: Robert Fryers, Blunham (GB); Stephen Russell Taylor, Melbourn (GB); Neil D'Souza-Mathew, Cambridge (GB)

(73) Assignee: Novartis AG, Basel (CH)

( * ) Notice: Subject to any disclaimer, the term of this patent is extended or adjusted under 35 U.S.C. 154(b) by 253 days.

(21) Appl. No.: 15/348,741

(22) Filed: Nov. 10, 2016

(65) Prior Publication Data

US 2018/0129070 A1    May 10, 2018

(51) Int. Cl.
*G02C 7/04* (2006.01)
*A61F 2/16* (2006.01)
(Continued)

(52) U.S. Cl.
CPC .......... *G02C 7/041* (2013.01); *A61F 2/1624* (2013.01); *G02B 7/28* (2013.01); *G02C 7/083* (2013.01);
(Continued)

(58) Field of Classification Search
CPC .......... G02C 7/04; G02C 7/083; G02C 7/101; G02C 7/049; G02C 11/10; G02C 2202/20; G02C 2202/16; G02C 7/022; G02C 2202/22; G02C 2202/18; G02C 7/02; G02C 7/081; G02C 7/08; G02C 7/061;
(Continued)

(56) References Cited

U.S. PATENT DOCUMENTS

| | | |
|---|---|---|
| 2006/0095128 A1 | 5/2006 | Blum et al. |
| 2009/0105817 A1 | 4/2009 | Bretthauer et al. |

(Continued)

FOREIGN PATENT DOCUMENTS

| | | |
|---|---|---|
| DE | 102005038542 A1 | 2/2007 |
| EP | 2754386 | 7/2014 |

(Continued)

*Primary Examiner* — Evan P Dzierzynski
*Assistant Examiner* — Sharrief I Broome
(74) *Attorney, Agent, or Firm* — Baker Botts L.L.P.

(57) ABSTRACT

A lens system comprises a first electro-active lens comprising a first focus sensor coupled to a first processor and a second electro-active lens comprising a second focus sensor coupled to a second processor. The first focus sensor periodically generates electromagnetic signals and detects electectromagnetic signals generated by the second focus sensor. The second focus sensor periodically generates electromagnetic signals and detects electectromagnetic signals generated by the second focus sensor. The first processor receives an indication of the second electromagnetic signals and, based on the received indication of the second electromagnetic signals, determines a relative convergence angle between the first and second electro-active lenses. Based on the determined relative convergence angle, the first processor determines a focal setting for the first electro-active lens and controls an electroactive element in the first electro-active lens, based on the determined focal setting.

14 Claims, 5 Drawing Sheets

(51) Int. Cl.
  *G02B 7/28* (2006.01)
  *G02C 7/08* (2006.01)
  *G02F 1/29* (2006.01)
(52) U.S. Cl.
  CPC .......... *G02F 1/29* (2013.01); *G02F 2001/294* (2013.01); *G02F 2201/58* (2013.01)
(58) Field of Classification Search
  CPC .......... G02C 7/085; G02C 7/044; G02C 7/06; G02C 7/102; G02C 2202/12; G02C 7/041; H01L 2924/00; H01L 2924/0002; H01L 2924/00014; H01L 2224/13109; H01L 2224/48091; H01L 2924/10253; H01L 2224/48145; H01L 2924/00012; H01L 2924/0105; H01L 2924/013; H01L 2224/11312; H01L 2224/16225; H01L 2224/2919; H01L 2224/32225; H01L 2224/45139; H01L 2224/73204; H01L 2224/83203; H01L 23/58; H01L 2924/01015; H01L 2924/01047; G02B 1/043; G02B 27/017; G02B 3/0081; G02B 7/28; G02B 7/285; G02B 2027/011; G02B 2027/0123; G02B 2027/0178; G02B 26/06; G02B 27/0172; G02B 27/0075; G02B 3/08; G02B 3/14; G02B 15/00; G02B 17/0808; G02B 23/06; G02B 26/0875; G02B 27/2235; G02B 27/646
  See application file for complete search history.

(56) References Cited

U.S. PATENT DOCUMENTS

| | | |
|---|---|---|
| 2010/0110379 A1 | 5/2010 | Zhou et al. |
| 2010/0324408 A1 | 12/2010 | Klink et al. |
| 2013/0027655 A1* | 1/2013 | Blum .................... G02C 7/083 349/193 |
| 2013/0245754 A1 | 9/2013 | Blum et al. |
| 2013/0261744 A1* | 10/2013 | Gupta .................. A61B 5/0031 623/6.22 |
| 2013/0338767 A1 | 12/2013 | Mazzocchi et al. |
| 2014/0148899 A1* | 5/2014 | Fehr ...................... A61F 2/1624 623/6.22 |
| 2016/0081793 A1* | 3/2016 | Galstian ................. G02C 7/04 351/159.03 |

FOREIGN PATENT DOCUMENTS

| | | | |
|---|---|---|---|
| EP | 2772791 A1 | 9/2014 | |
| WO | 2007/020184 | 2/2007 | |
| WO | 2008/009471 | 1/2008 | |
| WO | 2008/101898 | 8/2008 | |
| WO | 2010/076337 | 7/2010 | |
| WO | 2014/194432 A1 | 12/2014 | |
| WO | WO-2014194432 A1 * | 12/2014 | ............... G02C 7/04 |
| WO | 2015/165584 | 11/2015 | |
| WO | 2015/171773 | 11/2015 | |
| WO | 2017/015327 A1 | 1/2017 | |

* cited by examiner

CONVERGENCE-SENSING ELECTRO-ACTIVE ACCOMMODATING LENS

FIELD

The present disclosure relates generally to automatically-focusing intraocular lenses and contact lenses.

BACKGROUND

Electro-active lenses may comprise intraocular lenses (IOL) or contact lenses that include electronic components to control a portion of the lens's refractive power, prismatic power or tinting. Intraocular lenses (IOLs), for example, may be implanted in patients' eyes either to replace a patient's crystalline lens or to complement the patient's crystalline lens. In most cases, an IOL implanted during cataract surgery is a monofocal lens, typically set for distance vision. IOLs may also include multifocal lenses, which provide both distance vision as well as focus or near distances. Accommodating IOLs capable of changing focus based on muscular movement have also been proposed. However, conventional multifocal lenses and accommodating lenses do not operate as well as a natural crystalline lens.

Automatically-focusing electronic IOL and contact lenses have been proposed, but present technical challenges. One challenge concerns the mechanism for initiating accommodation. Convergence sensing is one possible approach for addressing this. According to the principle of convergence, when a patient focuses on a specific target, the lines of sight from the two eyes intersect at that target, and the angle between the two lines of sight is essentially inversely proportional to the distance from the patient to the object. Thus, sensors may be used to determine the correct focus point for that lens, i.e., the distance from the patient to the object of regard. Providing such sensors presents its own challenges, however.

Some have advocated convergence sensing via a magnetic field using internal magnets implanted in each IOL to establish orientation relative to the an external magnetic field (i.e., terrestrial magnetic field), and then to communicate the independent orientation back and forth between the two lenses to calculate the relative angle between lenses. Among other drawbacks, this approach incurs a large electrical power demand, which is difficult to provide in a limited volume implant. In addition, for certain head orientations this approach may not work, and implanting a magnet may not be practical due. While some have proposed additionally incorporating an accelerometer to address this issue, that solution results in complex, relatively large, implementation that shares many of the flaws in the magnet-based system.

Accordingly, improved methods, systems, and components for determining a correct focus point for an electro-lens system are needed.

BRIEF SUMMARY

Certain embodiments provide an electro-active lens system, comprising a first electro-active lens comprising a first focus sensor coupled to a first processor and a second electro-active lens comprising a second focus sensor coupled to a second processor. The first focus sensor is configured to periodically generate first electromagnetic signals and detect second electectromagnetic signals generated by the second focus sensor. The second focus sensor is configured to periodically second generate electromagnetic signals and detect first electectromagnetic signals generated by the second focus sensor. The first processor is configured to receive an indication of the second electromagnetic signals detected by the first focus sensor, based on the received indication of the second electromagnetic signals, determine a relative convergence angle between the first and second electro-active lenses, based on the determined relative convergence angle, determine a focal setting for the first electro-active lens, and control an electroactive element in the first electro-active lens, based on the determined focal setting for the first electro-active lens.

In certain embodiments, the second processor is configured to receive an indication of the first electromagnetic signals detected by the second focus sensor, based on the received indication of the first electromagnetic signals, determine the relative convergence angle between the first and second electro-active lenses, based on the determined relative convergence angle, determine a focal setting for the second electro-active lens, control an electroactive element in the second electro-active lens independent of the first electro-active lens, based on the determined focal setting for the second electro-active lens.

In certain embodiments, a frequency of the first and second electromagnetic signals is less than 50 MHz, such that the first and second electromagnetic signals behave as magnetic fields. The first and second focus sensors may each comprise at least two coils, which may be nonparallel.

In certain embodiments, the coils in each of the first and second focus sensors are energized to generate a fixed-direction magnetic field. In other embodiments, the at least two coils in each of the first and second focus sensors may be energized with an alternating current (AC) to produce a first and second rotating magnetic field, thereby generating respective first and second electromagnetic signals. In such embodiments, the magnetic fields sweep across multiple angles. Further, the first or second rotating magnetic field may be produced by combining a low-frequency sine and cosine modulation signal with a higher frequency carrier signal, and applying the combined signal to the coils such that the magnetic field alternates at a frequency of the carrier signal and rotates at a frequency of a modulation signal. In addition, the first or second rotating magnetic field may be produced by applying a first signal to a first one of the coils and a second signal to a second one of the coils, wherein the first and second signals each have a variable frequency and a constant amplitude. The first signal may have an increasing frequency and the second signal may have a decreasing frequency.

In certain embodiments, the coils are driven with direct current (DC).

In certain embodiments, the relative convergence angle between the first and second electro-active lenses is determined without digital communication between the electro-active lenses.

In certain embodiments, wherein the first focus sensor is configured to determine a gaze angle of the first lens, and wherein the first focus sensor determines a relative convergence angle between the first and second electro-active lenses only when the determined gaze angle is within a predetermined range.

In certain embodiments, the focal setting is calculated as optical power (D) based on the convergence angle Φ by:

$$\text{Optical Power}(D) = \frac{2\sin\left[\frac{\phi}{2}\right]}{P - 2C\sin\left[\frac{\phi}{2}\right]}$$

Certain embodiments may provide one or more technical advantages. For example, embodiments of the present disclosure may provide an accommodating lens system in which each lens is capable of directly measuring a relative convergence angle, thereby eliminating the need for complex and power-consuming digital eye-to-eye communication. Moreover, this may be accomplished using physical hardware (e.g., transmitters/receivers, ASICs, and power sources)

Embodiments may also provide sufficient measurement range and accuracy to ensure high-quality vision over the complete range of working distances. Certain embodiments may enable two lenses to compare convergence angles frequently without consuming a large amount of power.

DETAILED DESCRIPTION

Exemplary embodiments described below relate to a method and system for determining a correct focus point for an electro-active accommodating lens system based on convergence sensing via magnetic fields, and automatically focusing the electro-active lens. Although many of the examples herein focus on IOLs, it is understood that the principles and techniques apply analogously to automatic-focusing contact lenses.

The following description is presented to enable one of ordinary skill in the art to make and use the invention and is provided in the context of a patent application and its requirements. Various modifications to the exemplary embodiments and the generic principles and features described herein will be readily apparent. The exemplary embodiments are mainly described in terms of particular methods and systems provided in particular implementation, though the methods and systems will operate effectively in other implementations. Phrases such as "exemplary embodiment," "one embodiment" and "another embodiment" may refer to the same or different embodiments. Various embodiments are described with respect to systems and/or devices having certain components. However, the systems and/or devices may include more or less components than those shown, and variations in the arrangement and type of the components may be made without departing from the scope of the invention. Exemplary embodiments are also be described in the context of particular methods having certain steps, though the method and system operate effectively for other methods having different and/or additional steps and steps in different orders that are not inconsistent with the exemplary embodiments. Thus, the present invention is not intended to be limited to the embodiments shown, but is to be accorded the widest scope consistent with the principles and features described herein.

Figure 1:
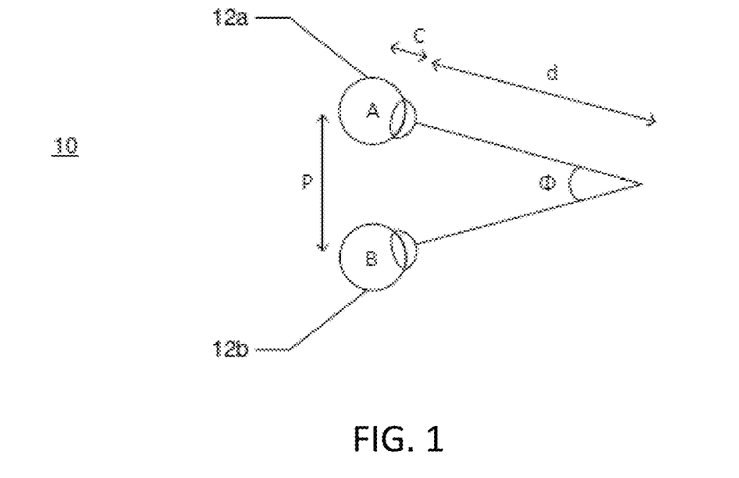
FIG. 1 is a diagram illustrating one embodiment of a system for determining a correct focus point for an electro-active accommodating lens system.

FIG. 1 is a block diagram illustrating a system for determining a focus point for an electro-active accommodating lens system, according to certain embodiments. The system 10 may include at least two electro-active accommodating lenses 12a and 12b (collectively referred to as electro-active lenses 12)—one for each eye A and B, as shown. Each of the electro-active lenses 12 may comprise an intraocular lens (IOL) or a contact lens. The lenses may change focus automatically (accommodate), and contain components that may be varied by electrical control, such as focusing elements. When someone using lenses 12a and 12b focuses on a specific target, the lines of sight from the user's eyes intersect at that target. The angle Φ between the two lines of sight is essentially inversely proportional to the distance from the patient to the object. Accordingly, the focus of the lenses may be controlled automatically based on the principle of convergence, i.e., determining a relative convergence angle Φ between two lines of sight of the two eyes using known trigonometric principles, and using the angle Φ to determine the correct focus point and optical power for the lenses.

To that end, one or more focus sensors of each electro-active lens 12 may periodically generate/transmit an electromagnetic signal. Each electromagnetic signal will produce a characteristic magnetic field (which may be a fixed-direction field or may rotate, as discussed further below). When two different magnetic fields are produced at a source at two different known angles from position A (e.g., by each of two focus sensors on lens 12a, arranged at different angles with respect to one another), the field vector(s) detected and measured at position B (e.g., one or more focus sensors on lens 12b) can be used to calculate the relative position and angle of positions A and B. The focus sensor(s) of each electro-active lens is therefore configured to detect the electromagnetic signals (or magnetic fields) from the contralateral lens, and each lens can determine a relative convergence angle between the two lenses based on the detected signals/fields. Each electro-active lens then uses the relative convergence angle to determine a correct focal setting and may set the focus accordingly.

Figure 2:
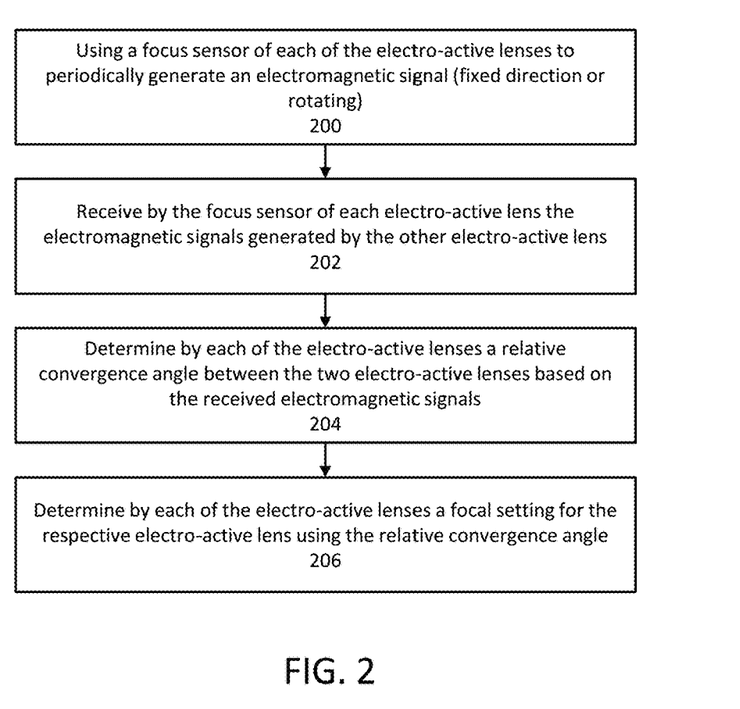
FIG. 2 is a flow diagram of one embodiment for a process of automatically determining a correct focus point for an electro-active lens system.

FIG. 2 is a flow diagram illustrating a process for automatically determining a correct focus point for an electro-active lens system 10 based on these principles. The process, described further below, includes using a focus sensor of each of the electro-active lenses to periodically generate an electromagnetic signal, which may be a fixed direction or rotating signal. The process further includes receiving, by the focus sensor of each electro-active lens, the electromagnetic signals generated by the other electro-active lens. Each of the electro-active lenses can then determine, using known algorithms based on known trigonometric principles, a relative convergence angle between the two electro-active lenses based on the received electromagnetic signals. Finally, each electro-active lens may determine a focal setting using the relative convergence angle.

Figure 3:
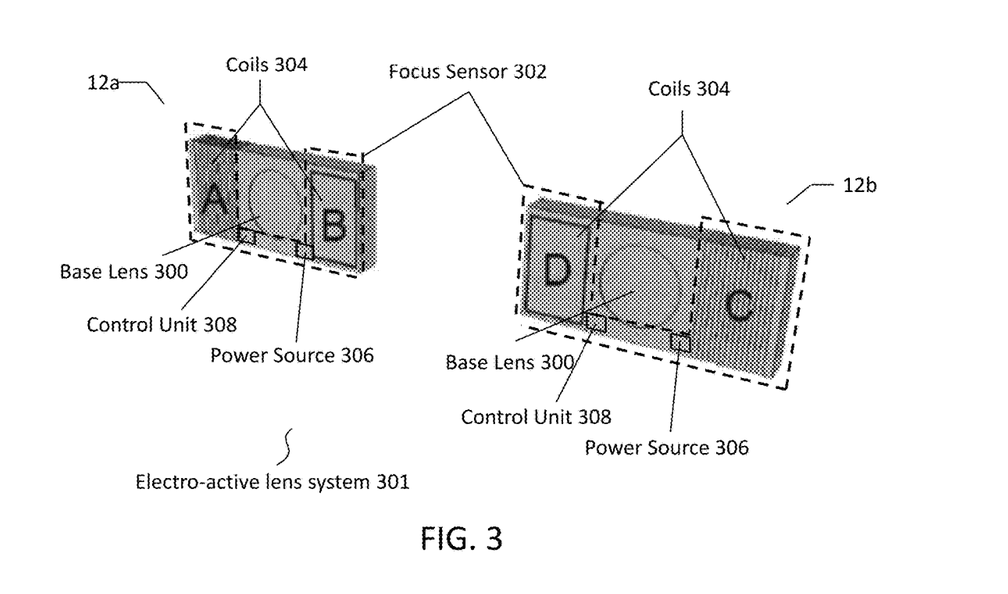
FIG. 3 is a diagram illustrating electro-active lenses in an exemplary embodiment.
Figure 5:
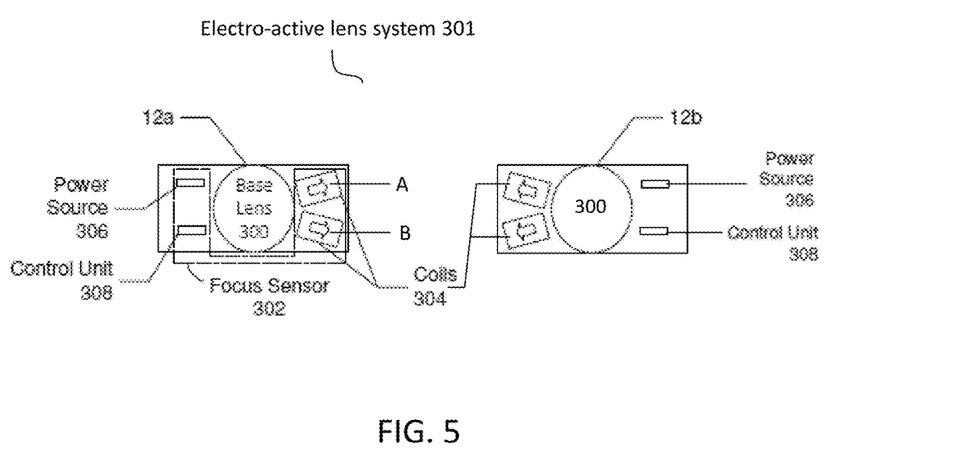
FIG. 5 is a diagram illustrating electro-active lenses in an exemplary embodiment.

FIGS. 3 and 5 illustrate examples of an electro-active lens system 301, each having components (like numbers referring to like components) which operate together and are configured to perform the processes illustrated in FIG. 2 and described herein. FIGS. 3 and 5 are not to scale, and the placement, sizes, and shapes of elements in system 300 may vary depending on the application.

FIGS. 3 and 5 each depict a system 301 which includes two electro-active accommodating lenses (e.g., IOLs) 12a and 12b each includes a base lens 300, a focus sensor 302 comprising two coils 304, a control unit 308 coupled to the focus sensor 302, and a power source 306 coupled to the focus sensor 302 and the control unit 308. In certain embodiments, the focus sensor 302 may comprise the two coils 304, as well as the control unit 308 and optionally the power source 306, as shown by the dashed lines. Control unit 308 includes one or more processors and a memory configured to execute instructions to direct and control processes and functions performed by focus sensor 302 (and subcomponents thereof), including the processes set forth in FIG. 2 and described herein. A processor may include one or more microprocessors, field-programmable gate arrays (FPGAs), controllers, application-specific integrated circuits (ASICs), or any other suitable computing devices or resources, and memory may take the form of volatile or non-volatile memory including, without limitation, magnetic media, optical media, random access memory (RAM), read-only memory (ROM), removable media, or any other suitable memory component. Memory may store instructions for programs and algorithms that, when executed by a processor, implement the functionality described herein with respect to any such processor, memory, or component that includes processing functionality.

In an eye-to-eye RF communication system that uses an angle measurement, directionality in transmit and receive components may be required to determine the convergence angle. In certain embodiments, directionality sensing is provided by using nonparallel coils 304 in the focus sensor 302 of each electro-active lens 12. For example, in FIG. 3, coils A and B of lens 12i a l are arranged orthogonally to one another, as are coils C and D of lens 12b. In contrast, coils 304 shown in FIG. 5 are angled with respect to one another, but are not orthogonal. These examples are provided for illustration, but in various embodiments the coils may be arranged according to any suitable angle, or even parallel (in the case a rotating magnetic field is used). In embodiments that use a fixed direction magnetic field, the coils of each lens 12a and 12b are nonparallel.

Focus sensors 302 provide direction sensing using an eye-to-eye radio frequency (RF) communication system. Coils 304 in one lens 12a may be used to both transmit and receive the electromagnetic signals to/from the other lens 12b. The control unit 308 may be programmed to measure the convergence angle based on electromagnetic signals detected by and received from coils 304 and to determine a focal setting using the convergence angle. In a further embodiment, the control unit 308 may optionally control a focus mechanism (not shown) for the base lens 300 to adjust the focus of base lens 300 according to the determined focal setting. The focus of base lens 300 may be adjusted using any suitable technique, such as electro-wetting or liquid crystal. The power source 306, which provides a power to the coils 304 and the control unit 308, may comprise a variety of micro form factors, as known in the art.

Accurate direction sensing may require compatibility with communications protocol(s), minimal background noise, minimal multipath reflections (as this may affect field pattern) and minimal distortion of the field pattern by human tissue. In certain respects, a magnetic field may be preferable to an electric field to achieve these points. For example, a magnetic field has shorter range (less interference from outside), less reflection, and tissue has negligible effect on magnetic fields, which is not true of an electric field. Rather than using magnets for producing such magnetic fields (which would render the IOLs unsuitable for magnetic resonance imaging), exemplary embodiments include a focus sensor that emits low frequency electromagnetic signals to determine the convergence angle between the pair of electro-active lenses 12. At the small distances involved in an electro-active lens system 301, such low frequency electromagnetic waves may behave as AC magnetic fields, as the electric field components are negligible. However, the frequency should be high enough to minimize the impact of external fields. Signal attenuation characteristics of tissue (and in particular tissues in the human head) are also pertinent to optimal frequency selection.

Moreover, a low duty cycle magnetic field may be desirable to reduce average power consumption, but transmission duration impacts accuracy and average power consumption. Shorter transmissions typically require higher power, though short, high-power transmissions may optimally balance average-power and accuracy in certain embodiments. Yet another factor to consider are limits on human RF exposure levels.

Based on these considerations, in certain embodiments of the invention coils 304 of focus sensor 302 transmit and receive low frequency electromagnetic signals that are preferably less than 50 MHz. In another embodiment, the electromagnetic signals may be in the range of 13-20 MHz, or may be approximately 13.56 MHz. In yet other embodiments, the electromagnetic signals may be in the range of or 1-2 MHz, 1-10 MHz, or 10-15 MHz. In certain embodiments, transmit periods may be shorter than 1 ms every 0.5 seconds, though any suitable duty cycle may be used based on power consumption and accuracy requirements. In certain embodiments, the duty cycle may be variable based on operating conditions. Accordingly, various embodiments can generate fields of acceptable levels with components small enough for implantation in an IOL or contact lens.

Returning to FIG. 2, at step 200, the coils 304 of each focus sensor are used to generate electromagnetic signals/fields, as noted above. In certain embodiments, a rotating magnetic field may be generated; in others, a fixed direction (non-rotating) magnetic field may be generated.

At step 202, the focus sensor(s) 302 of each electro-active lens 12 detects and receives the electromagnetic signals/magnetic fields generated by the other electro-active lens 12. In certain embodiments, each electro-active lens 12a and 12b may independently detect a magnetic field using two or more coils 304. Signals indicating the detected field may be sent to and received by control unit 308.

At step 204, each electro-active lens 12 determines a relative convergence angle between the two electro-active lenses based on the received signals/fields. As noted above, signals indicating a detected magnetic field may be received by a control unit 308, which includes a microprocessor configured to generate vector components of the detected field and calculate the angle of convergence 1 based on known trigonometric principles. Accordingly, in certain embodiments, the convergence angle between the two electro-active lenses may be determined by each lens 12 without digital communication between contralateral lenses.

At step 206, each electro-active lens may determine a focal setting for the respective electro-active lens based on the relative convergence angle. Referring again to FIG. 1 for example, control unit 308 may calculate (for the lens 12 with which it is associated) a focal setting as optical power (D) based on the convergence angle Φ according to the formula:

$$\text{Optical Power}(D) = \frac{2\sin\left[\frac{\phi}{2}\right]}{P - 2C\sin\left[\frac{\phi}{2}\right]}$$

Variables P and C may be pre-stored or programmed in memory of the control unit 308 based on individual characteristics of a patient/user. In some embodiments, such variables may be set and updated at or after the time the electro-active lenses are inserted into a patient's eye, based on actual measurements of the patient, via wireless communication with a transceiver and processor located on the electro-active lens. Such variables may be set or configured in any other suitable manner, as well.

Based on the calculated focal setting, the control unit 308 of each lens 12 may generate signals to cause the base lens 300 to accommodate to the appropriate focal setting using known techniques (e.g., electro-wetting, liquid crystal, etc.). Accordingly, various embodiments provide an improved technique for measuring convergence and automatically adjusting the focus of a lens.

It is noted that various factors may impact the measurement performance of each lens 12. For example, different patients will have different geometric parameters (e.g., interpupillary distance), and implanted lenses may be at different angles with respect to one another. Build tolerances are also introduce variability, and cyclotorsion of the eyes can impact device accuracy. Accordingly, certain embodiments of control unit 308 include calibration capabilities. For example, convergence measurements by lenses 12 when a patient is viewing targets of known distances may be recorded and used to calibrate system 301 to optimize accuracy. Calibration may be repeated whenever appropriate as part of a diagnostic evaluation. Other calibration requirements which may be required intermittently may be automated. For instance, embodiments of control unit 308 may automatically calibrate to account for battery levels (voltage changes) and potential drift of electronic components of the system.

Certain embodiments of control unit 308 may be configured to determine not only convergence angle (the relative angle between lenses 12 ), but also gaze angle (the average angle of the eyes with respect to 'straight ahead,' the horizontal line that bisects the lens). Large gaze angles may present performance challenges and decrease system accuracy. Moreover, computation of convergence angles at large gaze angles may not be physiologically appropriate. Accordingly, in certain embodiments control unit 308 may improve system performance and efficiency by selectively updating convergence angle information only when the gaze angle is within a predetermined range.

FIG. 3 illustrates an example of a coil alignment for certain embodiments of a convergence sensing system that use a fixed-direction magnetic field. In this example, the coils A and B may be energized sequentially to generate/transmit a magnetic field (e.g., coil A followed by coil B) having a suitable frequency and duty cycle, and the coils on the other lens (e.g., C and D) may be used as receivers to measure the field strength. In certain embodiments, coils 304 may be excited by a fixed-amplitude carrier frequency and may be energized sequentially (e.g., A then B) during a transmission cycle. While coils A and B are in the transmission cycle, coils C and D may be in a receive cycle, and may measure a received energy at the carrier frequency to calculate relative positioning of the lens (and convergence).

Figure 4:
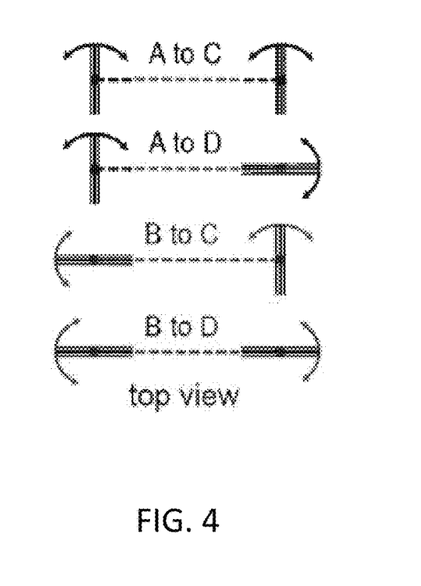
FIG. 4 is a diagram illustrating transmit-receive combinations among four coils in an electro-active lens system, according to certain embodiments.

Accordingly, the coils on one lens may transmit while the coils on the other lens listen. The measured signal level will vary with the relative angle between the lenses and coils. In this way, lens 12b having coils C and D can compute its angle with respect to lens 12a having coils A and B. Then, the process may be reversed, with coils C and D being energized while coils A and B are used to measure and compute the angle. In this arrangement, there are four transmit-receive combinations (A-C, A-D, B-C, and B-D), as shown in FIG. 4. That is, coils C and D can transmit to, and measure signals received from, coils A and B. Likewise, coils A and B can transmit to, and measure signals received from, coils C and D. Accordingly, each lens 12a and 12b can take four simultaneous measurements to calculate relative positioning. It is noted that, although FIG. 3 depicts coils A and B at 0° and 90° with respect to the long axis of the lens 12, other (non-orthogonal) angles may be used in various embodiments.

Additionally, although two coils are shown here on each lens 12, other embodiments may include a third coil to provide the ability to measure additional degrees-of-freedom and further improve system performance. For example, certain embodiments may include three coils A, B, and C on a first lens 12a and three additional coils X, Y, and Z on a second lens 12b. The coils on each lens may each be oriented at different relative angles (e.g., coil A at 0°, coil B at 45°, and coil C at 90°; likewise for X, Y, and Z). In this manner, coils A, B, and C may each transmit to and receive from coils X, Y, and Z, and vice-versa, enabling each lens may take up to nine simultaneous measurements (e.g., A-X, A-Y, A-Z, B-X, B-Y, B-Z, and C-X, C-Y, C-Z). One skilled in the art will appreciate that additional coils (more than three) may be included on each lens if additional measurements are desired.

Returning to FIG. 3, as noted above two different transmitter field angles at a source (e.g., lens 12a) are sufficient for measuring the angle between the two IOLs. The signal processing requirements for systems utilizing a static field approach are comparatively simple and efficient (particularly vis-à-vis the rotating field approach described below). Moreover, the number of signals being generated and overall power consumption is reduced. However, a significant reduction in measurement error is possible if a larger number of angles is measured, followed by performing averaging or regression analysis. Thus, in certain embodiments, a rotating electromagnetic field that sweeps across multiple angles is used to allow a continuum of data points for averaging and error compensation, hence the term "sweeping angle."

FIG. 5 illustrates an embodiment which may utilize a rotating magnetic field. In this example, nonparallel coils 304 may be driven (under the control of control unit 308 ) with an alternating current (AC) power supply to operate the coils 304 with AC excitation during transmission and produce a magnetic field with a rotating component. To minimize the power consumption, the resonant frequency of the coils 304 may be used.

In such embodiments, RF directionality may be provided through a beam steering method. In beam steering, the pair of coils 304 act as antennas where both of one lens's coils 304 transmit the electromagnetic signal with different phases (mini-phased array) and steer the electromagnetic signal (or radiation pattern beam) back-and-forth. The convergence angle may then be calculated by comparing the time when the signal is the maximum and minimum at the receiver to the time when the transmitted signal is maximum and minimum.

Two suitable methods of achieving beam steering or a rotating magnetic field may be termed 'AM' and 'FM' methods, as the principle of operation is similar to those of the methods of signal modulation in broadcast radio of the same names.

The AM method entails driving both coils 304 in phase at the same frequency, and varying the amplitudes on the coils at a lower modulation frequency. For example, a low frequency sine and cosine modulation signal may be mixed onto a higher frequency carrier signal. The carrier signal may be the resonant frequency of the coils 304 in certain embodiments. The modulation frequency of the carrier signal may be chosen to be low enough that simple, low power, electronics in the receiver lens can decode the signal but high enough so that DC signals (such as the Earth's magnetic field) can be filtered from the results reliably. Accordingly, in such embodiments, a magnetic field from the coils 304 of a source lens 12a alternates at the frequency of the carrier signal (the carrier frequency) and rotates at the frequency of the modulation signal (the modulation frequency). At the receiver lens 12b, a similar pair of coils 304 is used to detect the magnetic field in two nonparallel directions. These signals are received and demodulated to by control unit 308 remove the carrier frequency, leaving the modulation frequency (AM demodulation). These signals are then processed by control unit 308 as described above.

Figure 6:
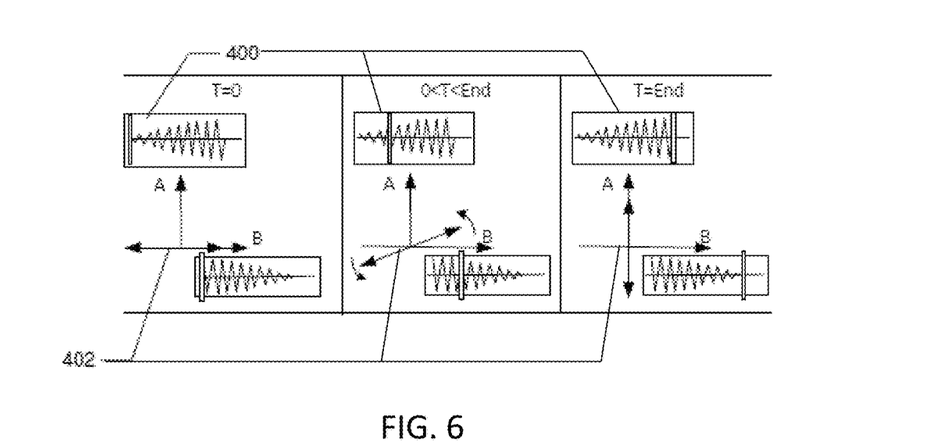
FIG. 6 is a block diagram graphically illustrating AM beam steering signal generation, according to certain embodiments.

FIG. 6 is a block diagram graphically illustrating AM beam steering signal generation. Representative waveforms 400 of the electromagnetic signals generated by both coils are shown in three timeslots—at time zero (t=0) on the left, a time between time zero and an end time (0<t<end) in the middle, and the end time (t=end) on the right. At t=0, the AC excitation is used to operate the coils 304 during transmission and produce a magnetic field with a rotating component 402, which starts aligned to one of the source coils (B). In the second timeslot, the transmitted AC magnetic field rotates at the modulation frequency. At t=end, the AC magnetic field is shown aligned to the other source coil (A).

Figure 7:
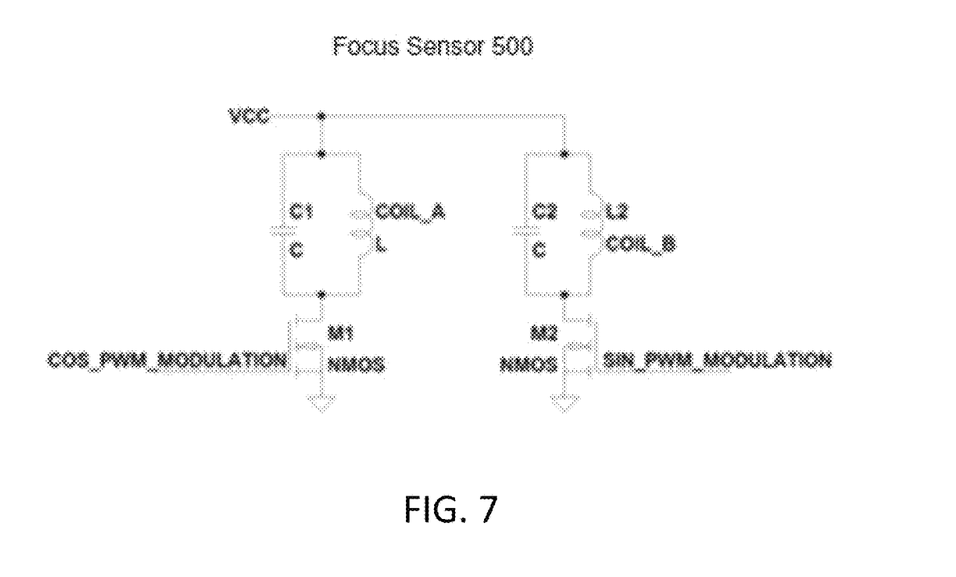
FIG. 7 is a diagram illustrating one embodiment of a focus sensor that may be used for AM beam steering, according to certain embodiments.

FIG. 7 is a diagram illustrating one embodiment of a focus sensor that may be used for AM beam steering. In this embodiment, the focus sensor 500 includes coils A and B that act as transmitters and are held in phase by oscillating LC resonator or tank circuits at a driven frequency. The tank circuits may comprise an inductor (L) and a capacitor (C) connected together and to a power-supply pin (VCC). In one embodiment, coil A includes NMOS logic for generating cosine pulse-width modulation (PWM) signals, and coil B includes NMOS logic for generating sine PWM signals. This arrangement allows sine and cosine modulation of the signals and requires processing to generate the PWM signals.

Figure 8:
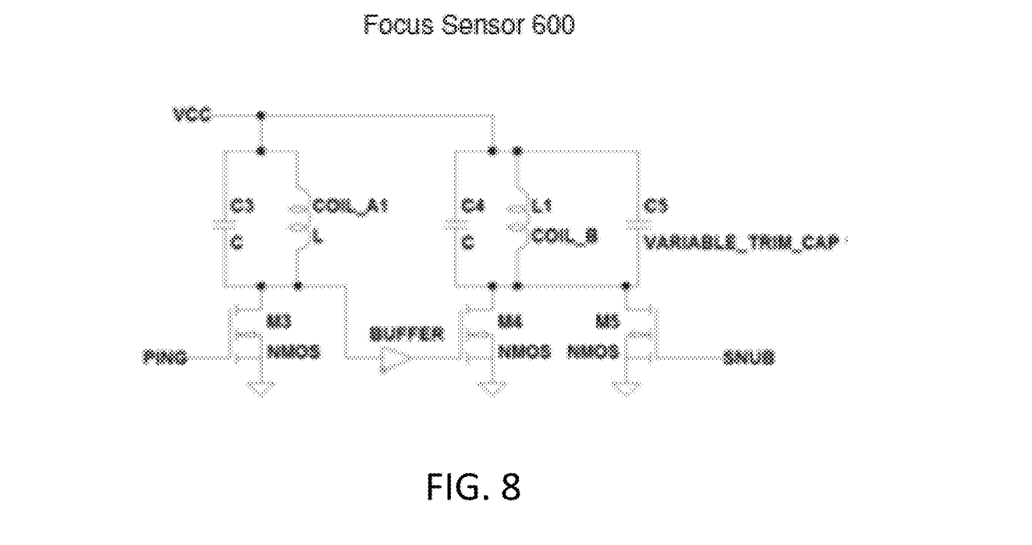
FIG. 8 is a diagram illustrating another embodiment of a focus sensor that may be used for AM beam steering.

FIG. 8 is a diagram illustrating another embodiment of a focus sensor that may be used for AM beam steering. In this embodiment, the focus sensor 600 is similar to the embodiment shown in FIG. 5, but slaves one LC resonator to the other, locking the phases together. The focus sensor 600 may be driven by simple digital input/output. The focus sensor 600 in this example produces decaying and rising exponential modulation, rather than sine and cosine.

Figure 9:
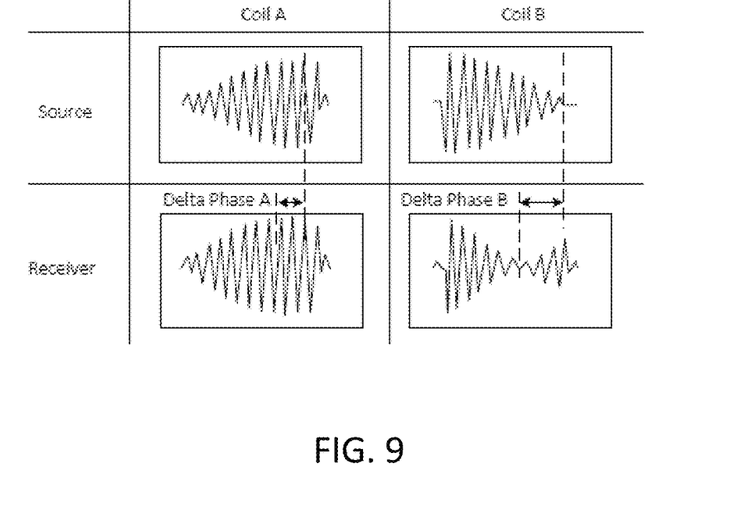
FIG. 9 is a diagram illustrating AM beam steering at a receiver, according to certain embodiments.

FIG. 9 is a diagram illustrating AM beam steering at a receiver. In one embodiment, the receiver may comprise an orthogonally-arranged pair of detectors (e.g., coils). The same pair of coils may be used for transmitting and receiving. Alternatively, receiving may be accomplished using a 2-axis GMR if the operating frequency is less than 2 MHz. Assuming coils are used, then operation at 13.56 MHz is possible. Receive coils A and B may detect the modulation at a phase delay (phase delay A for coil A and phase delay B for coil B), which depends on their position and orientation relative to the source. This phase delay varies as a function of convergence and direction and is different in each coil. Accordingly, phase delay for coils A and B may be plotted as a function of convergence angle for various gaze direction angles. Convergence and direction may thus be derived from phase delay.

Figure 10:
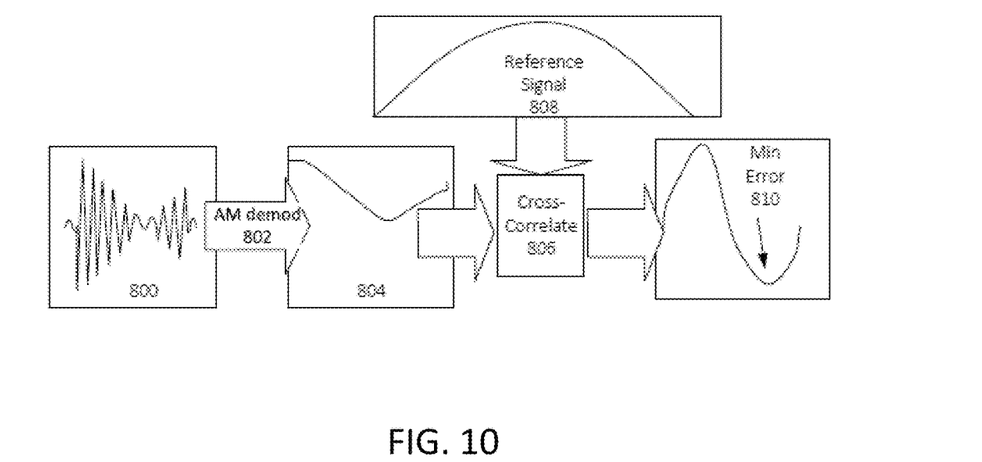
FIG. 10 is a diagram illustrating AM beam steering decoding at the receiver, according to certain embodiments.

FIG. 10 is a diagram illustrating AM beam steering decoding at the receiver. If the signal is too fast for low power electronics, it may be difficult or impossible to sample the raw electromagnetic signal at the receiving coils. Accordingly, the received signal 800 may be AM demodulated 802 followed by extraction of the modulation envelope 804. The modulation envelope 804 may be cross correlated 806 with a known reference signal 808 to measure differences in the phase of the modulation. Minimum error 810 identified in a cross correlation error function occurs when receive signal is in phase with the reference signal. This minimum error corresponds to the measurement.

Using a beam steering approach as described above may provide each lens 12 enough information to independently determine both direction and convergence angles. Accordingly, significant benefit of the approach above does not require transferring digital data between the IOLs to determine convergence. The beam carries position information of the other IOL and each IOL may alternate in the role of source and receiver.

An FM method for achieving beam steering may alternatively be used in certain embodiments. According to the FM method, frequencies of the two transmitter coils 304 from a source lens 12a are varied while constant amplitude is maintained. One transmitter coil may be driven with an increasing frequency and the other coil with a decreasing frequency. FM demodulation of the two signals detected on the two coils and received by the control unit 308 at the receiver lens 12b results in the same modulation signal for processing, as described above.

Accordingly, certain embodiments include a system that includes first and second electro-active lenses 12a and 12b, each comprising a focus sensor 302 coupled to a processor (e.g., in control unit 308). The focus sensor 302 of each lens (which may comprise a pair of nonparallel coils 304 as shown in FIG. 5) is configured to periodically generate electromagnetic signals using AM or FM modulation methods described above, and detect electectromagnetic signals generated by the other lens. The processor (in control unit 308) of each lens may be configured to independently receive an indication of the electromagnetic signals detected by the focus sensor 302, determine a relative convergence angle between the electro-active lenses 12a and 12b based on the indication, determine a focal setting for the electro-active lens 12a based on the determined relative convergence angle, and control an electroactive element to cause the electro-active lens to accommodate, based on the determined focal setting.

In an alternative embodiment, the two nonparallel transmitter coils 304 of each lens 12 may be driven with direct currents (DC) from a DC power supply. This results in a magnetic field emitted by the pair of transmitter coils 304 of a source lens 12a corresponding to an imaginary magnetic dipole, which is the vector sum of the two magnetic fields generated by the two transmitter coils 304. The ratio of the direct currents driving the two coils is varied over time to vary the angle of the resulting magnetic field. By varying the direct currents over time, the magnetic field can be made to rotate. In the specific case of varying the direct currents according to sine and cosine curves, the rotation (and transmission) of the magnetic field occurs at constant angular velocity—similar to the operation of the stator in a two pole, DC electric motor. In the receiver lens, a similar pair of nonparallel coils 304 independently detects the magnetic field strength. These provide two vector components of the magnetic field at the receiver lens 12b, which may be used by the control unit 308 to calculate the angle of actual magnetic field by simple trigonometry. This angle will vary as the transmitting field is rotated. If the range of angles that the transmitting lens sweeps through is known by design, and the range of received angles is measured, the angle between the two lenses can be calculated as simply the difference between these two ranges.

Thus, according to certain embodiments, focus sensor 302 may provide electro-active lenses with an electromagnetic signal having sufficient reliability on which to base an autofocus mechanism. Focus sensor 302 may utilize fixed-direction (non-rotating) or rotating magnetic fields, as described above. Certain embodiments provide several advantages over alternative approaches. For example, focus sensor 302 may provide a mechanism for each lens to directly measure the relative convergence angle without the need the need for potentially complex and power consuming digital eye-to-eye communication. This results in a simpler overall implementation with reduced power consumption. Examples of the focus sensor 302 also have potential for improved accuracy since a sufficient electromagnetic signal measurement range and accuracy is provided, ensuring high-quality vision over the full range of working distances. In addition, examples of focus sensor 302 rely on physical hardware (e.g., transmitter/receiver coils) that can be incorporated into dimensions suitable for inclusion on an electro-active lens. One skilled in the art will appreciate these and other advantages of the systems and techniques described herein.

The present invention has been described in accordance with the embodiments shown, and there could be variations to the embodiments, and any variations would be within the spirit and scope of the present invention. Accordingly, many modifications may be made by one of ordinary skill in the art without departing from the spirit and scope of the appended claims.

We claim:

1. An electro-active lens system, comprising:
a first electro-active lens comprising a first focus sensor coupled to a first processor;
a second electro-active lens comprising a second focus sensor coupled to a second processor; wherein:
the first focus sensor is configured to:
periodically generate first electromagnetic signals; and
detect second electectromagnetic signals generated by the second focus sensor;
the second focus sensor is configured to:
periodically second generate electromagnetic signals; and
detect first electectromagnetic signals generated by the second focus sensor;
the first processor is configured to:
receive an indication of the second electromagnetic signals detected by the first focus sensor;
based on the received indication of the second electromagnetic signals, determine a convergence angle between the first and second electro-active lenses;
based on the determined convergence angle, determine a focal setting for the first electro-active lens; and
control an electroactive element in the first electro-active lens, based on the determined focal setting for the first electro-active lens;
the second processor is configured to:
receive an indication of the first electromagnetic signals detected by the second focus sensor;
based on the received indication of the first electromagnetic signals, determine the convergence angle between the first and second electro-active lenses; and
based on the determined convergence angle, determine a focal setting for the second electro-active lens; and
control an electroactive element in the second electro-active lens independent of the first electro-active lens, based on the determined focal setting for the second electro-active lens; and
wherein
the first and second focus sensors each comprise at least two nonparallel coils;
the at least two coils in each of the first and second focus sensors are energized with an alternating current (AC) to produce a first and second rotating magnetic field, thereby generating respective first and second electromagnetic signals; and
the first or second rotating magnetic field is produced by combining a low-frequency sine and cosine modulation signal with a higher frequency carrier signal, and applying the combined signal to the coils such that the magnetic field alternates at a frequency of the carrier signal and rotates at a frequency of a modulation signal.

2. The system of claim 1, wherein a frequency of the first and second electromagnetic signals is less than 50 MHz, such that the first and second electromagnetic signals behave as magnetic fields.

3. The system of claim 1, wherein the coils in each of the first and second focus sensors are energized to generate a fixed-direction magnetic field.

4. The system of claim 1, wherein the magnetic fields sweep across multiple angles.

5. The system of claim 1, wherein the first or second rotating magnetic field is produced by applying a first signal to a first one of the coils and a second signal to a second one of the coils, wherein the first and second signals each have a variable frequency and a constant amplitude.

6. The system of claim 5, wherein the first signal has an increasing frequency and the second signal has a decreasing frequency.

7. The system of claim 1, wherein the coils are driven with direct current (DC).

8. The system of claim 1, wherein the convergence angle between the first and second electro-active lenses is determined without digital communication between the electro-active lenses.

9. The system of claim 1, wherein the first focus sensor is configured to determine a gaze angle of the first lens, and wherein the first focus sensor determines a convergence angle between the first and second electro-active lenses only when the determined gaze angle is within a range.

10. A method for determining a focus point for a pair of electro-active lenses, comprising:
   using a focus sensor of each of the electro-active lenses to periodically generate electromagnetic signals at a sweeping angle;
   receiving by the focus sensor of each respective electro-active lens the electromagnetic signals generated by the other electro-active lens;
   determining by each electro-active lenses a relative convergence angle between the two electro-active lenses based on the received electromagnetic signals; and
   determining by each of the electro-active lenses a focal setting for the respective electro-active lens using the relative convergence angle.

11. The method of claim 10, wherein the focus sensor comprises at least two nonparallel coils.

12. The method of claim 10, further comprising: energizing the coils to produce a fixed-direction magnetic field.

13. The method of claim 10, further comprising: energizing the coils with an alternating current (AC) to produce a rotating magnetic field.

14. The method of claim 10, wherein the focal setting is calculated as optical power (D) based on the convergence angle $\phi$ by:

$$\text{Optical Power}(D) = \frac{2\sin\left[\frac{\phi}{2}\right]}{P - 2C\sin\left[\frac{\phi}{2}\right]}.$$

* * * * *